US00PP24900P2

(12) United States Plant Patent

Ingemann Pedersen

(10) Patent No.: US PP24,900 P2
(45) Date of Patent: Sep. 16, 2014

(54) *LAVANDULA* PLANT NAMED 'TV4'

(50) Latin Name: *Lavandula stoechas*
Varietal Denomination: TV4

(75) Inventor: Jens Ingemann Pedersen, Odense N (DK)

(73) Assignee: BG Breeding APS, Odense (DK)

( * ) Notice: Subject to any disclaimer, the term of this patent is extended or adjusted under 35 U.S.C. 154(b) by 0 days.

(21) Appl. No.: 13/506,820

(22) Filed: May 17, 2012

(51) Int. Cl.
*A01H 5/00* (2006.01)

(52) U.S. Cl.
USPC ..... Plt./445

(58) Field of Classification Search
USPC ..... Plt./445
See application file for complete search history.

(56) References Cited

PUBLICATIONS

PLUTO Plant Variety Database Feb. 2013.*
Pluto Plant Variety Database search for TV4 May 2013. Page 1.*

* cited by examiner

*Primary Examiner* — Annette Para
(74) *Attorney, Agent, or Firm* — C. A. Whealy

(57) ABSTRACT

A new and distinct cultivar of *Lavandula* plant named 'TV4', characterized by its upright and somewhat outwardly spreading plant habit; freely branching habit; dense and bushy plant form; freely flowering habit; dark violet blue-colored flowers with long violet-colored terminal flower bracts; flowers arranged in compact verticillasters on crowded spike; and good garden performance.

2 Drawing Sheets

Botanical designation: *Lavandula stoechas.*
Cultivar denomination: 'TV4'.

BACKGROUND OF THE INVENTION

The present invention relates to a new and distinct cultivar of *Lavandula* plant, botanically known as *Lavandula stoechas* and hereinafter referred to by the name 'TV4'.

The new *Lavandula* plant is a product of a planned breeding program conducted by the Inventor in Cefane, South Africa. The objective of the breeding program was to develop new *Lavandula* plants with attractive flowers and relatively long flower bracts.

The new *Lavandula* plant originated from a cross-pollination made by the Inventor in September, 2005 of *Lavandula stoechas* 'Madrid Pink', not patented, as the female, or seed, parent with a proprietary selection of *Lavandula stoechas* identified as Clone 4, not patented, as the male, or pollen, parent. The new *Lavandula* plant was discovered and selected by the Inventor in November, 2006 as a single flowering plant from within the progeny of the stated cross-pollination in a controlled environment in Cefane, South Africa.

Asexual reproduction of the new *Lavandula* plant by terminal cuttings in a controlled greenhouse environment in Odense, Denmark since 2007 has shown that the unique features of this new *Lavandula* plant are stable and reproduced true to type in successive generations.

SUMMARY OF THE INVENTION

Plants of the new *Lavandula* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'TV4'. These characteristics in combination distinguish 'TV4' as a new and distinct *Lavandula* plant:

1. Upright and somewhat outwardly spreading plant habit.
2. Freely branching habit; dense and bushy plant form.
3. Freely flowering habit.
4. Dark violet blue-colored flowers with long violet-colored terminal flower bracts; flowers arranged in compact verticillasters on crowded spikes.
5. Good garden performance.

Plants of the new *Lavandula* differ from plants of the female parent, 'Madrid Pink', primarily in the length of the terminal flower bracts as plants of the new *Lavandula* have longer terminal flower bracts than plants of 'Madrid Pink'. In addition, plants of the new *Lavandula* and 'Madrid Pink' differ in flower color.

Plants of the new *Lavandula* differ from plants of the male parent selection primarily in the size of the inflorescences and terminal flower bracts as plants of the new *Lavandula* have longer inflorescences and terminal flower bracts than plants of the male parent selection.

Plants of the new *Lavandula* can be compared to plants of *Lavandula stoechas* 'Green Summer', disclosed in U.S. Plant Pat. No. 21,683. Plants of the new *Lavandula* and 'Green Summer' differ primarily in the following characteristics:

1. Plants of the new *Lavandula* are more vigorous and grow faster than plants of 'Green Summer'.
2. Plants of the new *Lavandula* are more upright than and are not as broad as plants of 'Green Summer'.
3. Plants of the new *Lavandula* have longer terminal flower bracts than plants of 'Green Summer'.

Plants of the new *Lavandula* can be compared to plants of *Lavandula stoechas* 'Early Summer', disclosed in U.S. Plant Pat. No. 22,273. Plants of the new *Lavandula* and 'Early Summer' differ primarily in the following characteristics:

1. Plants of the new *Lavandula* are larger than plants of 'Early Summer'.
2. Plants of the new *Lavandula* have longer lateral branches and internodes than plants of 'Early Summer'.
3. Plants of the new *Lavandula* flower later than plants of 'Early Summer'.
4. Plants of the new *Lavandula* have longer terminal flower bracts than plants of 'Early Summer'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph at the top of the first sheet comprises a side perspective view of a typical flowering plant of 'TV4' grown in a container.

The photograph at the bottom of the first sheet is a close-up view of a typical flowering stem of 'TV4'.

The photograph at the top of the second sheet is a close-up view of a typical inflorescence of 'TV4'.

The photograph at the center of the second sheet is a close-up view of typical terminal flower bracts of 'TV4'.

The photograph at the bottom of the second sheet is a close-up view of the upper surface of a typical leaf of 'TV4'.

DETAILED BOTANICAL DESCRIPTION

The aforementioned photographs, following observations and measurements describe plants grown during the summer in two-liter containers in an outdoor nursery in Odense, Denmark and under cultural practices which approximate those generally used in commercial *Lavandula* production. Plants were 23 weeks old when the photographs and description were taken. During the production of the plants, day temperatures ranged from 15° C. to 27° C. and night temperatures ranged from 3° C. to 15° C. In the following description, color references are made to The Royal Horticultural Society Colour Chart, 2007 Edition, except where general terms of ordinary dictionary significance are used.

Botanical classification: *Lavandula stoechas* 'TV4'.

Parentage:

*Female, or seed, parent.*—*Lavandula stoechas* 'Madrid Pink', not patented.

*Male, or pollen, parent.*—Proprietary selection of *Lavandula stoechas* identified as Clone 4, not patented.

Propagation:

*Type.*—Terminal vegetative cuttings.

*Time to initiate roots, winter.*—About 16 to 18 days at 20° C.

*Root description.*—Fine, fibrous.

Plant description:

*Plant and growth habit.*—Herbaceous perennial subshrub; upright and outwardly spreading plant habit; broad inverted triangle; moderately vigorous growth habit; freely branching habit, pinching enhances lateral branch development, dense and bushy plant form.

*Crop time.*—After rooting, about 20 weeks are required to produce finished flowering plants in two-liter containers.

*Plant height.*—About 30 cm.

*Plant width (spread).*—About 30 cm to 35 cm.

*Lateral branch description.*—Length: About 14 cm to 18 cm. Diameter: About 2 mm. Internode length: About 1.5 cm to 2 cm. Strength: Strong. Aspect: Upright to somewhat outwardly spreading. Texture: Tomentose, wooly. Color, immature: Close to 144B. Color, mature: Close to N199B.

*Foliage description.*—Arrangement: Opposite, simple; sessile. Length: About 2.8 cm to 3.5 cm. Width: About 4 mm. Shape: Lanceolate. Apex: Acute. Base: Cuneate. Margin: Entire, revolute. Texture, upper and lower surfaces: Pubescent. Fragrance: Aromatic, pungent. Venation pattern: Pinnate. Color: Developing leaves, upper surface: Between N138C and 191A. Developing leaves, lower surface: Close to N138C. Fully expanded leaves, upper surface: Close to 189A; venation, close to 189A. Fully expanded leaves, lower surface: Close to 191A; venation, close to 191B.

Flower description:

*Flower arrangement and shape.*—Single sessile flowers arranged in compact verticillasters on crowded spikes; freely flowering habit; flowers tubular with a two-lobed upper lip and a three-lobed lower lip and relatively long showy terminal flower bracts.

*Natural flowering season.*—Long flowering period; flowering continuous from the spring through the summer in Denmark.

*Flower longevity on the plant.*—Longevity of individual flowers is highly dependent on weather conditions; flowers not persistent; terminal flower bracts persistent.

*Fragrance.*—None detected.

*Flower buds.*—Length: About 7 mm. Diameter: About 2 mm. Shape: Oblong. Color: Close to N92C.

*Inflorescence size.*—Height: About 3 cm to 4 cm. Diameter: About 1.5 cm.

*Flowers.*—Diameter: About 1 cm. Depth (height): About 6 mm.

*Petals.*—Lip length: About 2 mm. Lip width: About 1 mm to 2 mm. Lip shape: Roughly spatulate to oval. Lip: Rounded. Lip margin: Entire. Lip texture, upper and lower surfaces: Smooth, glabrous. Lip color: When opening and fully opened, upper surface: Close to N92C; tube, white. When opening and fully opened, lower surface: Close to N92C; tube, white.

*Terminal flower bracts.*—Quantity and arrangement: About four in a single whorl at inflorescence apex. Length: About 3.5 cm to 4 cm. Width: About 1 cm to 1.2 cm. Shape: Obovate. Apex: Obtuse. Base: Cuneate. Margin: Entire, undulate. Texture, upper and lower surfaces: Pubescent. Color: Immature, upper and lower surfaces: Close to 83C; venation, close to 83A to 83B. Mature, upper and lower surfaces: Close to 83C; venation, close to 83A to 83B.

*Flower bracts.*—Arrangement: Each whorl of flowers subtended by a single flower bract. Length: About 1 cm. Width: About 1 cm. Shape: Broadly rhomboidal. Apex: Broadly acute. Base: Cuneate. Margin: Entire. Texture, upper surface: Tomentose, wooly. Texture, lower surface: Smooth, glabrous. Color, upper and lower surfaces: Close to 143D; venation, close to 143A.

*Sepals.*—Arrangement: Five sepals fused into a tube. Length: About 8 mm. Width: About 2 mm. Shape: Lanceolate. Apex: Four have acute apices; the apex of the fifth sepal is rounded to cordate. Margin: Entire. Texture, upper and lower surfaces: Tomentose, wooly. Color, upper and lower surfaces: Close to 143B; towards the base, lighter than 143B.

*Peduncles*.—Length: About 6 cm to 6.5 cm. Diameter: About 2 mm. Strength: Strong. Aspect: Mostly upright. Color: Close to 143B.

*Reproductive organs*.—Stamens: Quantity per flower: Four. Anther shape: Reniform. Anther length: About 0.5 mm. Pollen amount: Scarce. Pollen color: Yellow orange. Pistils: Quantity per flower: One. Pistil length: About 5 mm. Stigma shape: Club-shaped. Stigma color: Dark purple. Style length: About 4 mm. Style color: Whitish. Ovary color: Yellow green.

*Seeds*.—Length: About 3 mm. Diameter: About 2 mm.

Disease & pest resistance: Plants of the new *Lavandula* have not been noted to be resistant to pathogens and pests common to *Lavandula* plants.

Garden performance: Plants of the new *Lavandula* have exhibited good garden performance and to have good tolerance to rain and wind.

It is claimed:

1. A new and distinct *Lavandula* plant named 'TV4' as illustrated and described.

* * * * *

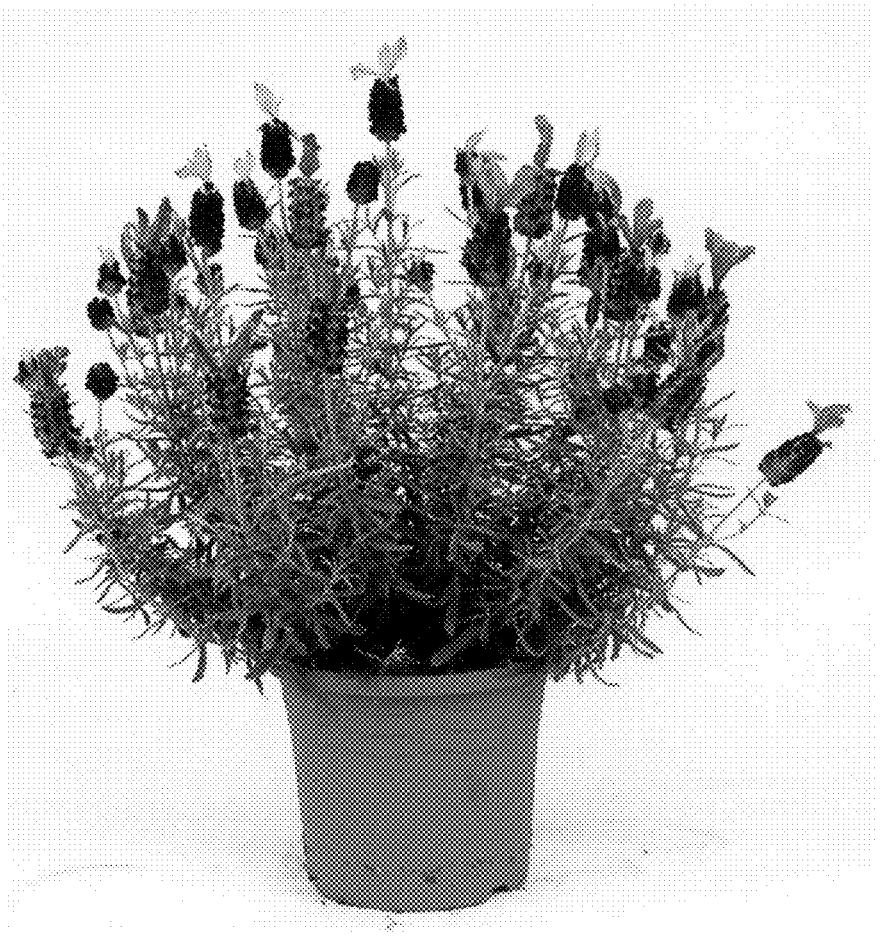
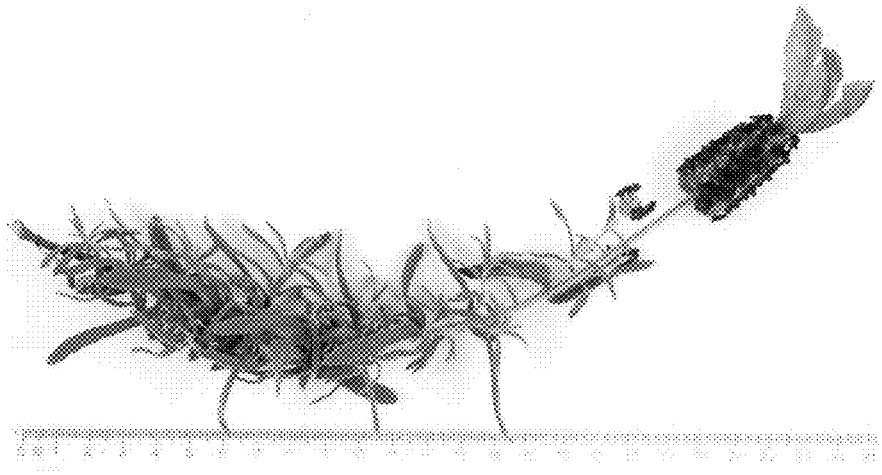

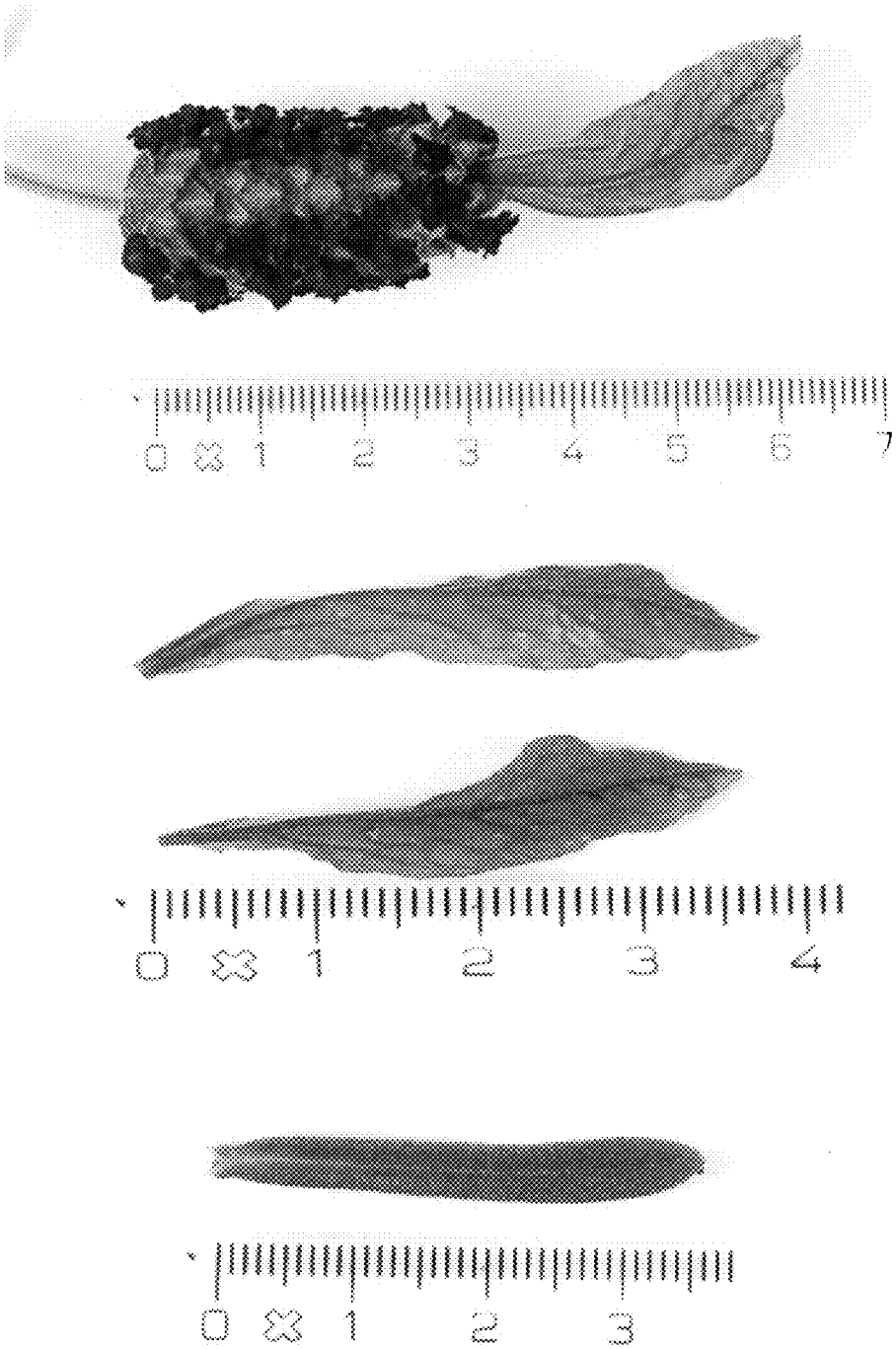
0 1 2 3 4 5 6 7
0 1 2 3 4
0 1 2 3